United States Patent
Ibnusaud et al.

[11] Patent Number: 6,127,553
[45] Date of Patent: Oct. 3, 2000

[54] CONVENIENT METHOD FOR LARGE-SCALE ISOLATION OF HIBISCUS ACID

[75] Inventors: Ibrahim Ibnusaud; Rani Rajasekharan; Teena Philip; Salini Thomas, all of Kottayam, India

[73] Assignee: Department of Science and Technology, Goverment of India, India

[21] Appl. No.: 09/365,300

[22] Filed: Jul. 30, 1999

[30] Foreign Application Priority Data

Aug. 3, 1998 [IN] India .................. 2249/DEL/98

[51] Int. Cl.[7] .................. C07D 305/12; C07D 307/02
[52] U.S. Cl. .................. 549/313; 549/295
[58] Field of Search .................. 549/313, 295

[56] References Cited

U.S. PATENT DOCUMENTS

| | | | |
|---|---|---|---|
| 4,005,086 | 1/1977 | Guthrie | 260/247.2 |
| 4,006,166 | 2/1977 | Guthrie | 260/343.6 |

OTHER PUBLICATIONS

Acta Chem. Scand. vol. 23, Per M. Boll et al, Jan. 1969.
Acta Chemica Scandinavica vol. 23 pp. 286–293,Per Boll et al, Naturally occuring Lactones and Lactames, Jun. 1969.
C. Martius et al.; Darstellung, physiologisches Verbaiten und Bedeutung der (+)–Oxycitronensaure und uhner Isonieren; Z.Physiol.Chem. 33, 1941, 269, pp. 33–40.
P.Boll, et al.; Naturally Occurring Lactones and Lactames; Aeta Chemn. Scand. 23 (1969) No. 1; pp. 286–293.
J. Herrmann; Method for Alkylating Lactones; JCS Chem.Comm. 1973; pp. 711–712.
Y.S. Lewis et al.; (–)–Hydroxycitric Acid—The Principal Acid in the Fruits of Garcini Cambogia Desr.; Phytochemistry, 1965, vol. 4; pp. 619–625.
S.Drioli et al.; Synthesis of (+)– and (–)–Phaseolinic Acid by Combination of Enzymatic Hydrolysis and Chemical Transformations with Revision of the Absolute Configuration of the Natural Product; J. Org. Chem. 1998, pp. 2385–2388.
E. Moret et al.; A Diastereoselective Synthesis of Both Quercus Lactone Isomers Employing Allyl–type Organometallics as Key Intermediates; Tetrahedron Letters vol. 25, No. 40; 1984; pp. 4491–4494.
J.Triscari et al.; Comparative Effects of (–) hydrosycitrate and (+)–allo–hydroxy–citrate on Acetyl CoA Carboxylase and Fatty Acid and Cholesterol Synthesis in Vivo; Lipids 1977, 12(4), pp. 357–363.
H. Brunengraber et al; Effect of (–)–hydroxy citrate on Ketone Production by the Perfused Liver; Lab.Chim. M. Univ. Libra Brusceller, Brusceller, Brussels, Belg. FEBS Lett. 1976, 65 (2), pp. 251–253.

*Primary Examiner*—Alan L. Rotman
*Assistant Examiner*—Rita Desai
*Attorney, Agent, or Firm*—Norris, McLaughlin & Marcus P.A.

[57] ABSTRACT

The invention relates to a process for the isolation of Hibiscus acid or (+)hydroxycitric acid lactone (2S,3R-dihydroxy-1,2,3-propanetricarboxylic acid lactone) from the leaves of *Hibiscus furcatus, Hibiscus sabdariffa* and *Hibiscus cannabinus*. Garcinia acid, one of the optical isomers of hydroxycitric acid is a potentially interesting molecule and found extensive application in the pharmacological as well as synthetic fronts.

13 Claims, 3 Drawing Sheets

I

Ia: R = H

Ib: R = $CH_3$

Ic: R = $C_2H_5$

Ic: R = $C_2C_6H_5$

Ia: R = H

Ib: R = CH$_3$

Ic: R = C$_2$H$_5$

Ic: R = C$_2$C$_6$H$_5$

Scheme I $^{13}$C nmr spectrum of : δ 173.196, 172.316, 167.049, 82.942, 78,434 and 42.065 ppm.
Hibiscus acid
in acetone-d$_6$ Mass spectrum : m/z 191(M+1)(4), 172(1), 162(5), 145(59), 127(12),
of Hibiscus acid 116(37), 99(84), 88(100), 60(48), 55(28).

FIG. 3

CONVENIENT METHOD FOR LARGE-SCALE ISOLATION OF HIBISCUS ACID

BACKGROUND OF THE INVENTION

The invention relates to a process for the isolation of Hibiscus acid or (+)hydroxycitric acid lactone (2S,3R-dihydroxy-1,2,3-propanetricarboxylic acid lactone) from the leaves of *Hibiscus furcatus, Hibiscus sabdariffa* and *Hibiscus cannabinus*. Garcinia acid, one of the optical isomers of hydroxycitric acid is a potentially interesting molecule and found extensive application in the pharmacological as well as synthetic fronts.

REFERENCES

1. U.S. Pat. No. 4,005,086 dated Jan. 25, 197;
2. U.S. Pat. No. 4,006,166 dated Jan. 2, 1977;
3. CA 86, 1977 186629r;
4. CA 85, 1976, 41531x;
5. Tetrahedron Letters vol. 25, pp. 4491–4494, 1984;
6. J. Org. Chem. 63, 2385–2388, 1988;
7. JCS Chem. Comm. pp. 711, 1973). However only very little information is available on Hibiscus acid (Ia), another optical isomer of hydroxy citric acid. The potential of the molecule is not yet explored due to the non-availability of the compound in the market. There is no economically viable large-scale isolation procedure available for this compound. Though Y. S. Lewis & S. Neelakantan (Phytochemistry. vol 4, pp 619–624, 1965) describes the presence of hibiscus acid in the leaves of *Hibiscus furcatus* and *Hibiscus cannabinus,* no method is reported on the isolation of the acid in large scale. Hence the present invention assumes importance.

Existing Methods a. The method reported by Per. M. Boll, Else Sorensen and Erik Balieu (Acta Chem. Scand 23 pp. 286–293, 1969) for the isolation of Hibiscus acid is from the calyx of the fruits of *Hibiscus sabdariffa*. In this method dried, ground calyxes of *Hibiscus sabdariffa* fruits are extracted at room temperature for 68 hours several times with methanol containing 1.5% hydrogen chloride. To the pooled methanol extracts, ether is added and the coloring matter is deposited as a dark red syrupy mass. Ether layer is collected and syrup is dissolved in methanolic hydrogen chloride (1%) and again precipitated by the addition of ether. The pooled ether extracts are evaporated and is dissolved in methanol. Upon cooling colorless crystals are obtained and the same is recrystallised from propanol.

b. Another method for the laboratory-scale production of hibiscus acid described by Martius, C. and Laue, R. (Z. Physiol. Chem. 33, 1941, 269) is purely a synthetic one. In this method Hibiscus acid is prepared from a number of chemical constituents and not from any natural source.

Drawbacks of prior arts

The drawbacks of the existing method "a" are:

1. The method fails to get pure Hibiscus acid when the leaves of the plants are used and in applicable only in case of the calyxes of *Hibiscus sabdariffa*.

2. *Hibiscus sabdariffa*. is a seasoned flowering plant and hence the calyxes may not be available at any given time.

3. Large quantities of expensive solvent other is required for the process.

4. Crystallization was effected only on prolonged (2 months) storage over drierite, in a desiccater.

The drawbacks of the existing method "b" are:

Method "b" describes the synthesis of Hibiscus acid from chemical constituents and is not economically viable.

Advantages of the new method

The present invention is novel and general process for the isolation of Hibiscus acid from the fresh or dried leaves or calyxes of *Hibiscus furcatus, Hibiscus sabdariffa* and *Hibiscus cannabinus*.

The method is economic, simple and less time consuming.

The leaves of the above plants are available through out South India in all seasons.

This method can be scaled up for large-scale isolation of Hibiscus acid.

The availability of Hibiscus acid at a reasonable rate in the market may prompt researchers to use this compound extensively for pharmaceutical and synthetic applications. Crystals of Hibiscus acid is isolated in the optically pure form in a faster and simple way.

BRIEF DESCRIPTION OF THE DRAWINGS

FIG. 3 shows the mass 13-C nmr and mass spectrometry data for Hibiscus acid of the invention.

DETAILED DESCRIPTION OF THE INVENTION

Figure 1:
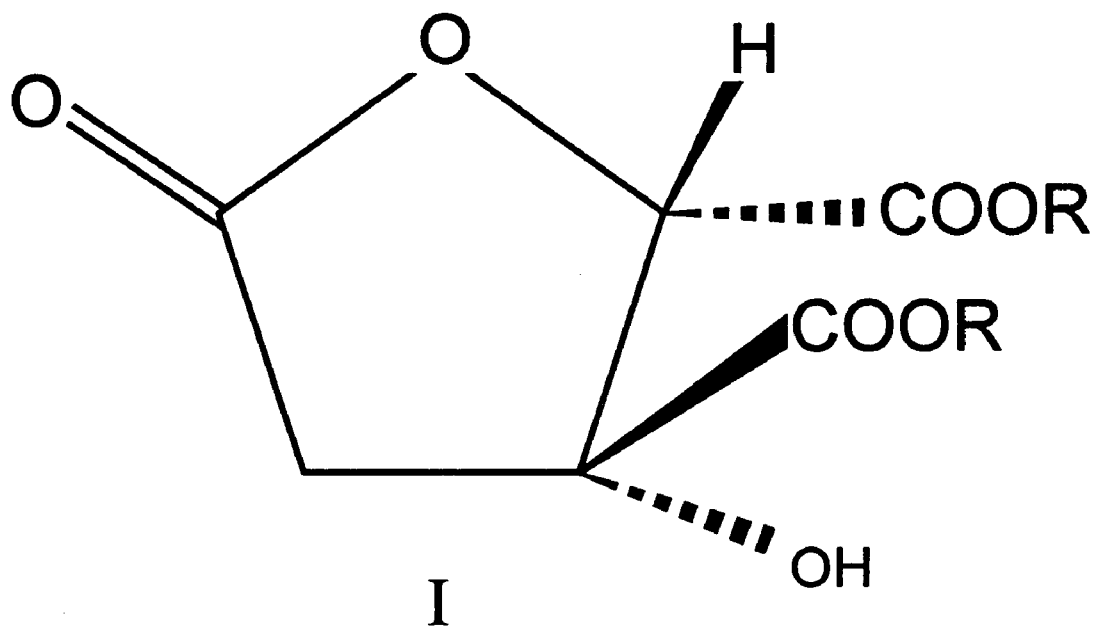
FIG. 1 is chemical formula showing Hibiscus acid and homologs thereof.
Figure 2:
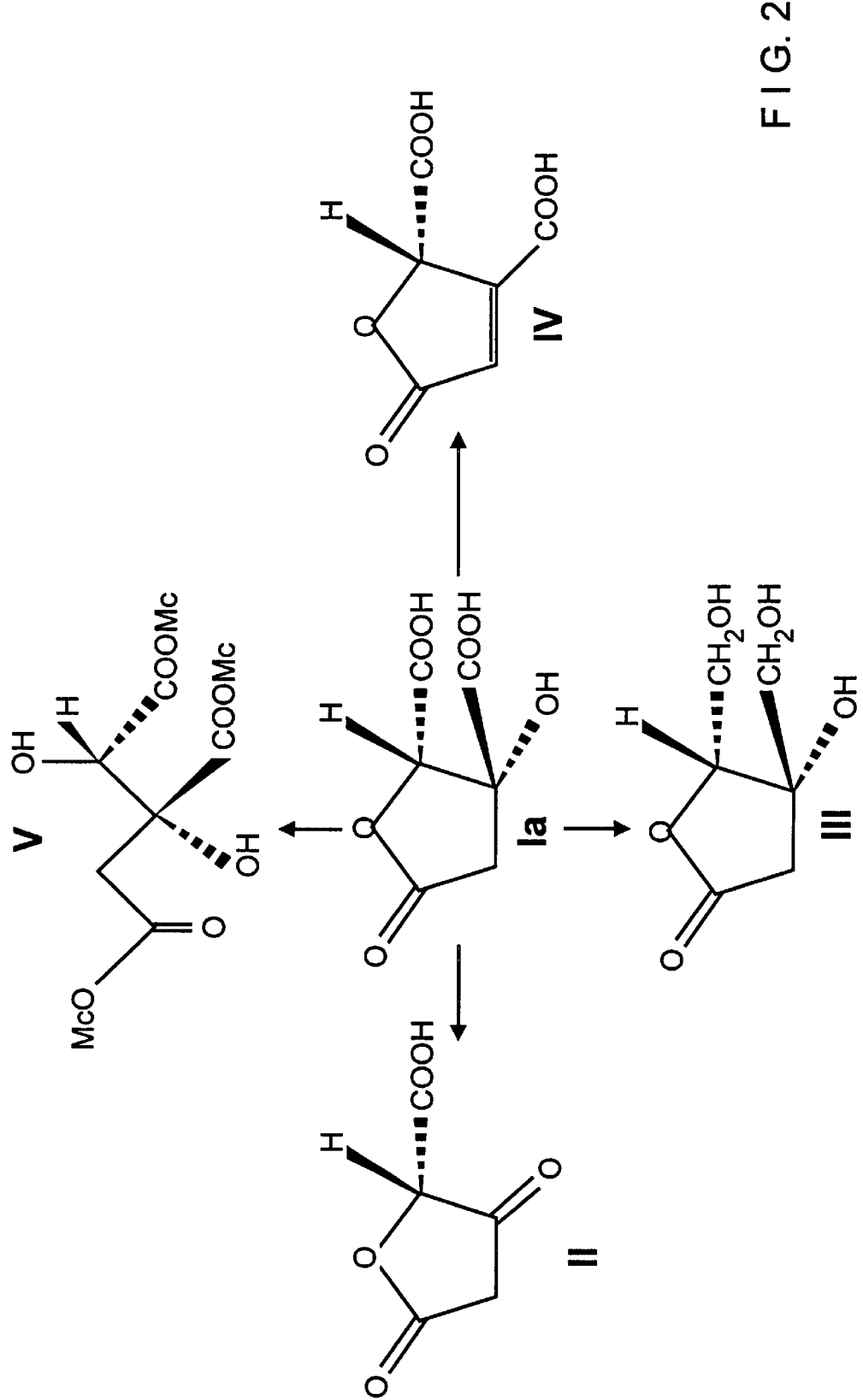
FIG. 2 shows the chemical formula of Hibiscus acid, and formulas for compositions derived as reaction products thereof.

1. Fresh or dried leaves of *Hibiscus furcatus, Hibiscus sabdariffa* or *Hibiscus cannabinus* are cut into small pieces and soaked in acidic alcohols like methanol, ethanol etc. for 12–36 hours and the extract is collected. The process is repeated many times and the combined extracts are concentrated to a thick syrup(A). Alternatively the leaves can be subjected to exhaustive soxhlet extracted with acidic alcohols like methanol, ethanol etc. to get the extract.

2. Sufficient water is used to precipitate organic impurities form syrup(A) and filtrate is concentrated to get syrup(B).

3. Syrup(B) is extracted with appropriate solvents like methanol, ethanol, acetone etc. several times and combined extracts on concentration gives a residue(C).

4. Residue (C) is extracted several times with suitable solvents like ethyl acetate, ether or chloroform. The extract on concentration furnished crude Hibiscus acid(D).

5. The crude Hibiscus acid(D) is further purified by converting it into ester (Ib) followed by acidic hydrolysis.

6. The purity of Hibiscus acid (Ia) isolated in step 5 is confirmed by spectroscopic and other physical data. The I R $^1$H-nmr, specific rotation, melting point are comparable with the reported values.

It may be noted that there are no data available on the $^{13}$C nmr and mass spectra of Hibiscus acid and its methyl ester. We have recorded the $^{13}$C nmr and mass spectra and the values are given below.

The $^{13}$C nmr spectra were recorded on Jeol GSX 400 spectrometer.

$^{13}$C nmr spectrum of :δ173.196, 172.316, 167.049, 82.942, 78.434 and 42.065 ppm. Hibiscus acid in acetone-d$_6$

*Mass spectrum :m/z 191(M+1)(4), 172(1), 162(5), 145 (59), 127(12), of Hibiscus acid 116(37), 99(84), 88(100), 60(48), 55(28).

$^{13}$C nmr spectrum of :δ172.742, 170.799, 166.139, 81.956, 77.903, 53.116, 53.025, Hibiscus acid 99(100) and 74 (25). dimethyl ester Functionalized furanones (Scheme I) are important building blocks in organic synthesis. These lactones are useful for the preparation of optically active ligands and for the synthesis of biologically active natural products. Hibiscus acid (Ia) isolated by the present method was effectively used for the preparation of Ib, Ic, Id, II, III, IV and V (Scheme I). These compounds were synthesized by the reaction of title compound (Ia), with methanol and acid (Ib), with ethanol and acid (Ic), with benzylalcohol and acid (Id), with oleium (II), with $BH_3$-THF (III), with HBr followed by elimination (IV)

with HBr in methanol (V)

The process is illustrated by the following example which should not be construed to limit the scope of the present invention.

EXAMPLE (a) Dried leaves of *Hibiscus furcatus* (1 Kg) were soaked in sufficient quantity of acidic methanol for 24 hours at room temperature. The extraction was repeated many times. The combined extracts were concentrated to a thick syrup and water was added until the organic impurities were precipitated completely. The clear filtrate was concentrated to a syrupy mass and was extracted with acetone many times. The acetone extracts were concentrated and finally extracted with ether several times. The combined ether extracts up on evaporation gave 15 g of crude product.

(b) Conversion of the crude product to dimethyl ester was done as given below.

(i) The crude compound (15 g) was treated with excess ethereal solution of diazomethane. The reaction mixture on concentration and filtration yielded 12 g colourless crystals of Hibiscus acid dimethyl ester (Ib).

Melting point: 129° C.

(ii) Alternatively 5 g of the crude product was refluxed with acidic methanol for a few hours. The reaction mixture was evaporated to a syrup and extracted with chloroform. On concentration of chloroform layer 2.5 g colourless crystals of Hibiscus acid dimethyl ester (Ib) were obtained.

Melting point: 128° C.

(c) Conversion of the ester to Hibiscus acid (Ia). The dimethyl ester (5 g) was refluxed with 3N HCl until the hydrolysis was complete and was concentrated under reduced pressure. The white solid obtained was dried under vacuum till hydrogen chloride was removed completely.

Melting point: 182° C. (decomp.) Yield: 4.0 g (91%)

We claim:

1. A process for isolation of Hibiscus Acid from the fresh or dried leaves and/or calyxes of *Hibiscus furcatus, Hibiscus sabdariffa* and/or *Hibiscus cannabinus,* comprising the steps of, in sequence:

(a) subjecting the leaves and/or calyxes to extraction using acidic alcohol to form an extract (b) adding water to said extract to remove organic impurities so as to form a filtrate.

(c) (1) subjecting the filtrate to further extraction using a non-acidic solvent chosen from the group consisting of methanol, ethanol and acetone to form a residue, (c) (2) subjecting the residue to extraction with one chosen from the group consisting of ethyl acetate, ether and chloroform, to form a crude Hibiscus acid (d) converting the crude to Hibiscus acid dimethyl ester, and (e) converting the ester by acid hydrolysis to Hibiscus acid lactone.

2. The process of claim 1, wherein in step (a), the leaves and/or calyxes are cut into small pieces and soaked in alcohol for 12–36 hours.

3. The process of claim 1, wherein step (a) is repeated a plurality of times, each with a new batch of leaves and/or calyxes, to provide a plurality of extract batches, said batches being combined and concentrated to form a thick syrup.

4. The process of claim 1, wherein in step (b), the impurities are removed by precipitation.

5. The process of claim 1, wherein in step (c), the filtrate is concentrated to form a syrupy mass prior to further extraction.

6. The process of claim 1, wherein step (c) further comprises evaporating to form a concentrated crude.

7. The process of claim 1, wherein said acidic alcohol of step (a) is methanol or ethanol.

8. The process of claim 5, wherein step (c) comprises concentrating the filtrate to form a syrupy mass, extracting said syrupy mass with a solvent chosen from the group consisting of methanol, ethanol and acetone, to form a residue.

9. The process of claim 8, wherein the residue is extracted with a solvent chosen from the group consisting of ethyl acetate, ether and chloroform, to form a crude.

10. The process of claim 1, wherein in step (a), the leaves and/or calyxes are cut into small pieces and subjected to exhaustive soxhlet extraction.

11. Hibiscus acid in optically-pure, crystal form.

12. The Hibiscus acid of claim 11, having $^{13}C$ nmr and mass spectral data as follows:

$^{13}C$ nmr spectrum of Hibiscus acid in acetone-$d_6$: δ173.196, 172.316, 167.049, 82.942, 78.434 and 42.065 ppm;

Mass spectrum of Hibiscus acid: m/z 191(M+1) (4), 172(1), 162(5), 145(59), 127(12), 116(37), 99(84), 88(100), 60(48), 55(28);

$^{13}C$ nmr spectrum of Hibiscus acid dimethyl and 40.138 ppm, ester in DMSO-$d_6$: δ172.742, 170.799, 166.139, 81.956, 77.903, 53.116, 53,025; and Mass spectrum of Hibiscus acid 99(100) and 74(25), dimethyl ester;

m/z 219(M+1) (6), 191(2), 159(100), 141(10), 130(38).

13. The process of claim 1, wherein the Hibiscus acid is isolated from fresh or dried leaves, and step (a) comprises subjecting the leaves to extraction using acidic alcohol to form an extract.

* * * * *